United States Patent [19]

Smith et al.

[11] 4,345,002
[45] * Aug. 17, 1982

[54] NOVEL INTUMESCENT COMPOSITION AND FLAME RETARDANT ARTICLES TREATED THEREWITH

[75] Inventors: Ray E. Smith, Lake Buena Vista, Fla.; Jayendra G. Shukla; Richard R. Nicholson, both of Ann Arbor, Mich.

[73] Assignee: Great Lakes Chemical Corporation, West Lafayette, Ind.

[*] Notice: The portion of the term of this patent subsequent to May 6, 1997, has been disclaimed.

[21] Appl. No.: 76,041

[22] Filed: Sep. 17, 1979

Related U.S. Application Data

[63] Continuation-in-part of Ser. No. 939,628, Sep. 5, 1978, abandoned.

[51] Int. Cl.³ .......................... C09D 5/18; D04H 1/58
[52] U.S. Cl. .................. 428/288; 106/18.15; 106/18.17; 252/602; 252/606; 252/607; 252/608; 428/378; 428/529; 428/531; 428/913; 428/921
[58] Field of Search .......................... 106/18.15, 18.17; 427/325; 428/921, 529, 531, 378, 288, 913; 252/606, 602, 607, 608

[56] References Cited

U.S. PATENT DOCUMENTS

| | | | |
|---|---|---|---|
| 3,077,458 | 2/1963 | Quelle et al. | 252/606 |
| 3,849,368 | 11/1974 | Anderson et al. | 252/609 X |
| 3,900,327 | 8/1975 | Miller | 106/18.17 X |
| 3,958,061 | 5/1976 | Singer et al. | 428/921 X |
| 3,980,618 | 9/1976 | Birum | 252/609 X |
| 4,110,513 | 8/1978 | Heitmann et al. | 252/607 X |
| 4,140,660 | 2/1979 | Den Otter et al. | 252/608 X |
| 4,201,677 | 5/1980 | Shukla et al. | 252/606 |

*Primary Examiner*—Richard D. Lovering
*Attorney, Agent, or Firm*—Kirkland & Ellis

[57] ABSTRACT

An intumescent composition containing a cyclic nitrogen compound, a hydroxy-containing organo-phosphorus compound, an organo-phosphorus acid, and water, wherein:
(a) said cyclic nitrogen compound is:

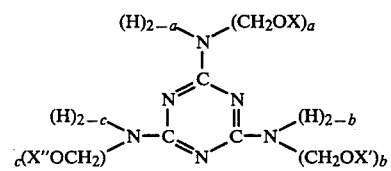

wherein a, b, and c, are integers selected from the group consisting of 1 and 2, a plus b plus c equal about 3 to 6, and wherein and X, X', and X" are hydrogen or —CH₃;
(b) said hydroxy-containing organo-phosphorus compound is selected from the group consisting of:

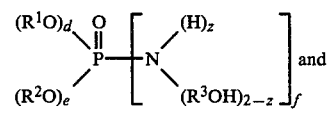

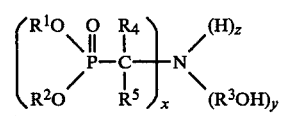

and mixtures thereof wherein $R^1$, $R^2$ and $R^3$ are lower alkyl or haloalkyl radicals and $R^4$ and $R^5$ are hydrogen, lower alkyl or haloalkyl radicals;
(c) said acid is selected from the group consisting of:

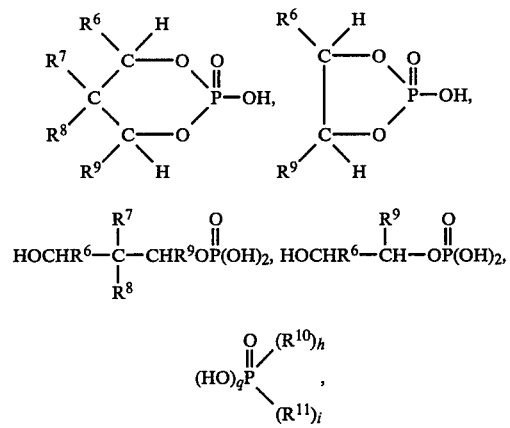

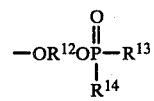

and mixtures thereof, wherein $R^6$, $R^7$, $R^8$ and $R^9$ are hydrogen, lower alkyl, haloalkyl or hydroxyalkyl, $R^{10}$ and $R^{11}$ are lower alkyl, haloalkyl, hydroxy-polyalkyleneoxy, alkoxy, hydroxyalkoxy or haloalkoxy, $$-OR^{12}O\overset{O}{\underset{R^{14}}{\overset{\|}{P}}}-R^{13}$$

wherein $R^{12}$ is lower alkylene, haloalkylene, polyalkyleneoxy, hydroxy-alkylene and $R^{13}$ and $R^{14}$ are hydrogen, hydroxyl, lower alkyl, hydroxy-polyalkyleneoxy, alkoxy, hydroxyalkoxy or haloalkoxy.

43 Claims, No Drawings

NOVEL INTUMESCENT COMPOSITION AND FLAME RETARDANT ARTICLES TREATED THEREWITH

CROSS REFERENCE TO RELATED APPLICATIONS

This application is a continuation-in-part of U.S. Patent Application Ser. No. 939,628, filed Sept. 5, 1978, and now abandoned.

BRIEF SUMMARY OF THE INVENTION

A novel intumescent composition containing methylated methylol melamine, an hydroxy-containing organo-phosphorus compound, an organo-phosphorous acid, and water.

DETAILED DESCRIPTION

It is difficult to impart durable flame retardance to a wood substrate. Wood substrates present a flameproofing problem which is materially different from that presented by fibrous hydrophilic organic substrates. According to U.S. Pat. No. 2,927,050 in the latter substrate " . . . substantially independent fibers are tangled together, leaving interstices capable of being filled by an aqueous medium by capillary action between all of their surfaces. The individual fibers contain a relatively small amount of cellulose, and the materials composed of them have a relatively low ignition temperature." In wood substrates, however, " . . . the cellulosic fibers are bonded together to form a relatively impenetrable block susceptible to little capillary action. A piece of wood has small surface area in relation to the amount of surface area it contains and has a relatively high ignition temperature." Because of these factors, " . . . a flameproofing agent which flameproofs fibrous hydrophilic organic materials is not likely to flameproof wood because its capacity to inhibit burning is likely to be destroyed by the time it is heated to the ignition temperature of the wood and/or because of the difficulty of causing a non-volatile substance to penetrate into the volume of a block of wood."

Impregnation of a wood substrate with a fire-retardant is known in the art. U.S. Pat. No. 3,398,019 teaches that this method must be used to impart a satisfactory degree of flame retardancy to wood fiber insulation, starting that "as far as is known only by the use of a chemical retardant which impregnates the board can a commercially acceptable building material be produced which is capable of securing a nonflammable rating." U.S. Pat. No. 4,049,849 teaches that this method, although well known, presents several substantial problems. According to this patent, the use of a wood substrate impregnated with a fire-retardant salt is restricted to low humidity applications " . . . due to the water solubility and hygroscopicity of most known fire retardant salts." Thus, " . . . if an ammonium phosphate-impregnated wood substrate is exposed to high (greater than 90 percent) humidity at ambient temperature, in approximately 3 days the fire retardant impregnant (salt) will leach therefrom . . . . The salt will absorb sufficient water vapor to enable it to migrate to the wood substrate surface. Not only does this leaching deplete the salt content of the wood substrate, rendering it less fire resistant, but it also severely disfigures the wood substrate's surface . . . . "

Many of the flame retardants which are used to impregnate wood substrates are acidic and hygroscopic. U.S. Pat. No. 3,811,992 teaches that the use of these compositions dehydrates the wood and that " . . . the wood, in order to make up for the dehydration caused by these hygroscopic agents, must absorb water from the moisture in the ambient air." Such moisture absorption will tend to discolor the plywood and rust and stain connecting members such as nails; and it " . . . dilutes the amount of agent used in the wood . . . and causes the wood to be damp and moist thus not only corroding the wood but subjecting it to attack from insects and the like . . . . "

Those in the art have attempted to impart durable flame retardance to wood substrates by applying intumescent compositions to them. Many intumescent compositions have been tested; U.S. Pat. No. 3,668,121 correctly states that only a few of them are of any value. Many of them produce excessive smoke and/or toxic gaseous pyrolysis products. According to U.S. Pat. No. 3,769,074, most of these prior art intumescent compositions are " . . . characterized by the disadvantages of high cost, low spreading rate, relatively poor efficiency, and poor weatherability". U.S. Pat. No. 3,513,114 teaches that prior art intumescent coating compositions " . . . exhibit the distinct disadvantage of either or both failing to maintain a coating film which will withstand repeated scrubbing or washing and thus exhibit wet abrasion resistant properties and/or failing to perform their intended function, that is, to intumesce, and thus fire retard after repeated scrubbing or washing". U.S. Pat. No. 3,535,130 teaches that " . . . conventional intumescent paints are usually sensitive to attack by water . . . . " U.S. Pat. No. 3,654,190 discloses that prior art intumescent compositions are water permeable and tend to degrade when exposed to moist environments.

U.S. Pat. No. 3,513,114 discloses that the problems presented by the prior art intumescent compositions cannot be solved merely by replacing the water soluble flame retardant agents they contain with water insoluble additives, for such substitution does not necessarily increase the wet abrasion resistance properties of the compositions. Furthermore, such a substitution will present a new set of problems if the water insoluble additive must be dissolved in an organic solvent; for many dangers are created by the use of the common organic solvents. Toluene, for example, is a fire hazard and an explosion hazard when exposed to heat and flame; and it emits toxic fumes. Methylene chloride is very dangerous to the eyes. Benzene is highly flammable, causes leukemia, and it is a known carcinogen. Acetone is a fire hazard when exposed to either heat or flame. Methanol possesses narcotic properties and exerts a toxic effect upon the nervous system; once it is absorbed into the body, it is eliminated very slowly and, thus, is a cumulative poison. The use of almost any of the common organic solvents will present some hazard.

U.S. Pat. No. 3,654,190 teaches that many prior art intumescent coating compositions are soft and "prone to chip with rough handling".

Other prior art considered by the applicants during the preparation of this application includes U.S. Pat. No. 2,711,998 (a composition containing trimethylol melamine and the ammonium salt of halopropyl phosphoric acid used to flame retard cotton), U.S. Pat. No. 2,676,162 (an intumescent coating for wood containing organic solvent, methylated methylol melamine, the reaction product of ammonia and phosphoryl chloride, and a film-forming condensation product), U.S. Pat.

No. 3,449,161 (fire-retardancy can be incorporated into paint compositions using organo-phosphorous amides), U.S. Pat. No. 3,635,970 (melamine phosphate is especially useful in intumescent paint compositions), U.S. Pat. No. 4,026,810 (an intumescent flame retardant prepared by reacting, e.g., phosphoric oxide, phosphoric acid, pentaerythritol, and melamine and thereafter curing the reaction product by heating to evolve gaseous products), U.S. Pat. No. 2,582,961 (an aqueous flame retardant for cellulosic fiber containing, e.g., methylated methylol melamine, methylol dicyandiamide, and an oxygen-containing acid of phosphorus), U.S. Pat. No. 2,661,342 (flameproofing of cellulosic materials with a resinous aminoplast condensation product such as melamine and a water-soluble nitrogen- and phosphorus-containing product), U.S. Pat. No. 3,023,176 (a water-soluble hardenable condensation product which is prepared by reacting a methylol compound of the aminotriazine group, an aliphatic compound containing a chain of at least 7 carbon atoms and a reactive hydrogen bound to a hetero atom, and a compound that is capable of introducing atomic groupings that raise the hydrophility in a non-ionic manner), U.S. Pat. No. 3,101,278 (methylol-phosphorus polymers which have nitrogen atoms incorporated into them are excellent flame retardants and are suitable for treating cellulosic materials), and U.S. Pat. No. 3,332,240 (an aqueous solution for flameproofing cotton fiber containing a salt of hydroxylamine and melamine resin).

It does not appear that the prior art describes an aqueous composition which can impart durable flame retardance to wood substrates even after repeated exposure to water, which will form a coating film which will withstand repeated scrubbing or washing, and which will substantially decrease the amount of noxious fumes generated during pyrolysis of the treated wood substrate.

Applicants have discovered a unique intumescent composition which is substantially superior to the prior art compositions. None of the individual ingredients of applicants' composition intumesce when exposed to an open flame; however, the coatings formed from this composition intumesce during pyrolysis.

In accordance with this invention, there is provided an intumescent composition containing a cyclic nitrogen compound, a hydroxy-containing organo-phosphorus compound, an organo-phosphorus acid, and water, wherein:

(1) said cyclic nitrogen compound is:

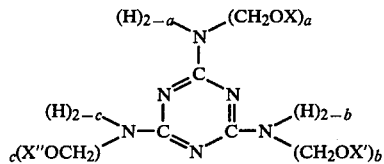

wherein a, b, and c are integers selected from the group consisting of 1 and 2, a plus b plus c equal to about 3 to 6, and X, X', and X'' are independently selected from the group consisting of hydrogen and —CH$_3$;

(2) said phosphorus compound is selected from the group consisting of:

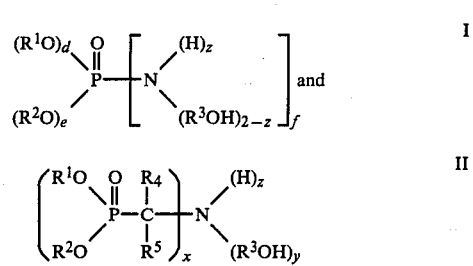

and mixtures thereof, wherein d is an integer of from 0 to 2, e is an integer of from 0 to 2, f is an integer of from 1 to 3, and d plus e and f equal 3; z is an integer of 0 to 1; x is an integer of 1 to 2, y is an integer of 1 to 2, and x plus y plus z equal 3; $R^1$, $R^2$, and $R^3$ are selected from the group consisting of alkyl radicals containing from about 1 to about 6 carbon atoms and haloalkyl radicals containing from about 2 to about 6 carbon atoms, provided that when $R^3$ is haloalkyl it contains at least 3 carbon atoms; $R^4$ and $R^5$ are selected from the group consisting of hydrogen, alkyl radicals, and haloalkyl radicals, wherein said radicals contain from about 1 to about 6 carbon atoms; and the total number of carbon atoms in the $R^1$, $R^2$, $R^3$, $R^4$, and $R^5$ groups does not exceed about 14; and (3) said acid is selected from the group consisting of:

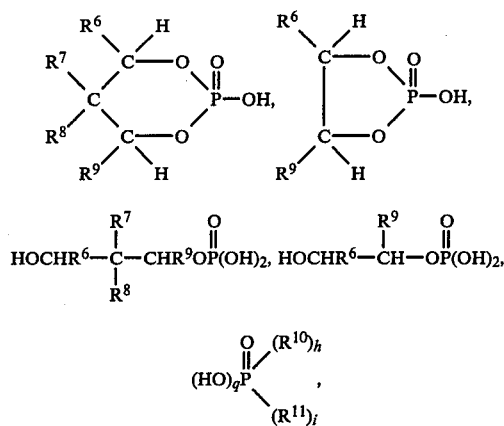

and mixtures thereof, wherein $R^6$, $R^7$, $R^8$ and $R^9$ are independently selected from the group consisting of hydrogen, alkyl of from about 1 to about 3 carbon atoms, haloalkyl of from about 1 to about 3 carbon atoms, and hydroxyalkyl of from 1 to about 3 carbon atoms, provided that the total number of carbon atoms in the $R^6$, $R^7$, $R^8$, and $R^9$ groups does not exceed about 5; wherein q is an integer of from 1 to 2, h and i are integers independently selected from the group consisting of 0, 1, and 2, and q plus h plus i equals 3; and wherein $R^{10}$ and $R^{11}$ are independently selected from the group consisting of alkyl of from about 1 to about 6 carbon atoms, haloalkyl of from about 1 to about 6 carbon atoms and from 1 to about 3 halogen atoms, hydroxy-polyalkyleneoxy containing 2 to 6 carbon atoms and 2 to 6 oxygen atoms, alkoxy of from about 1 to about 6 carbon atoms, hydroxyalkoxy of from about 2 to about 6 carbon atoms, haloalkoxy of from about 2 to about 6 carbon atoms and from about 1 to about 3 halogen atom,

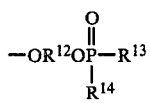

wherein $R^{12}$ is selected from the group consisting of alkylene of from about 2 to about 6 carbon atoms, haloalkylene of from about 3 to about 6 carbon atoms and from about 1 to about 3 halogen atoms, polyalkyleneoxy containing 2 to 6 carbon atoms and 1 to 5 oxygen atoms, and hydroxyalkylene of from 3 to about 6 carbon atoms and 1 to 4 hydroxyls, and $R^{13}$ and $R^{14}$ are independently selected from the group consisting of hydrogen, hydroxyl, alkyl of from about 1 to about 6 carbon atoms, haloalkyl of from about 1 to about 6 carbon atoms and from about 1 to about 3 halogen atoms, hydroxypolyalkyleneoxy containing about 2 to about 6 carbon atoms and 2 to B 6 oxygen atoms, alkoxy of from about 1 to about 6 carbon atoms, hydroxyalkoxy of from about 2 to about 6 carbon atoms, and haloalkoxy of from about 2 to about 6 carbon atoms and 1 to about 3 halogen atoms, provided that the total number of carbon atoms in the $R^{10}$ and $R^{11}$ groups does not exceed about 8.

The intumescent coating composition of this invention contains a cyclic nitrogen compound. It is preferred that this composition contain about 30 to about 60 percent (by weight) of said cyclic nitrogen compound. As used in this specification, the term "percent" refers to a weight percent; it is the ratio of the weight of the component involved divided by the combined weights of all the components involved times 100. Thus, e.g., the term "percent", when applied to the cyclic nitrogen compound, refers to the weight of the cyclic nitrogen compound times 100 divided by the combined weight of the cyclic nitrogen compound, the phosphorus compound, the acid, and the water.

The cyclic nitrogen compound used in the intumescent coating composition of this invention is described by the formula:

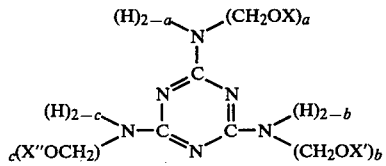

wherein a, b, and c are integers selected from the group consisting of 1 and 2, a plus b plus c equal about 3 to 6, and X, X', and X'' are independently selected from the group consisting of hydrogen and —CH$_3$. It is preferred that at least one of said X, X', and X'' groups be —CH$_3$. This cyclic nitrogen compound may be prepared by reacting at least three moles of formaldehyde per mole of melamine and then etherifying the methylol groups by reaction of the methylol melamine with methanol in the presence of an acid catalyst. Oligomers derived from said cyclic nitrogen compound also may be used in the intumescent composition of this invention.

In the more preferred cyclic nitrogen compound used in the intumescent composition of this invention, at least about two of said X, X', and X'' groups are —CH$_3$. In the most preferred embodiment, at least three of said X, X', and X'' groups are —CH$_3$.

It is preferred that from about 35 to about 50 percent (by weight) of said cyclic nitrogen compound be used in the intumescent composition of this invention. The trimethylated trimethylol melamine, tetramethylated tetramethylol melamine, pentamethylated pentamethylol melamine, and hexamethylated hexamethylol melamine compounds are all well known to the art; and all of them may be used in the intumescent composition of this invention. Mixtures of said compounds may also be used in the intumescent composition of this invention.

The intumescent composition of this invention also contains a phosphorus comound. It is preferred that said composition contain from about 10 to about 50 percent (by weight) of a phosphorus compound; it is more preferred that it contain from about 14 to about 40 percent (by weight) of said phosphorus compound.

It is preferred that the phosphorus compound used in the intumescent composition of this invention be selected from the group consisting of:

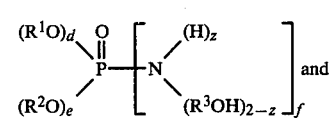  I

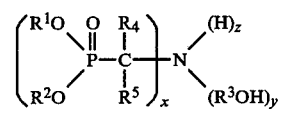  II and mixtures thereof, wherein d is an integer of from 0 to 2, e is an integer of from 0 to 2, f is an integer of from 1 to 3, and d plus e plus f equal 3; z is an integer of 0 to 1; x is an integer of 1 to 2, y is an integer of 1 to 2, and x plus y plus z equal 3; $R^1$, $R^2$, and $R^3$ are selected from the group consisting of alkyl radicals containing from about 1 to about 6 carbon atoms and haloalkyl radicals containing from about 2 to about 6 carbon atoms, provided that when $R^3$ is haloalkyl it contains at least 3 carbon atoms; $R^4$ and $R^5$ are selected from the group consisting of hydrogen, alkyl radicals, and haloalkyl radicals, wherein said radicals contain from about 1 to about 6 carbon atoms; and the total number of carbon atoms in the $R^1$, $R^2$, $R^3$, $R^4$, and $R^5$ groups does not exceed about 14.

In a preferred embodiment, the phosphorus compound is soluble in either the water and/or the acid components of the composition; in this preferred embodiment, when one part of the phosphorus compound is mixed with no more than one part of the component in which it is soluble at 25 degrees centigrade, a one-phase solution is obtained.

The phosphorus compounds described by formula I may be made by methods well known to the art. Thus, for example, some may be prepared in accordance with the following reaction scheme:

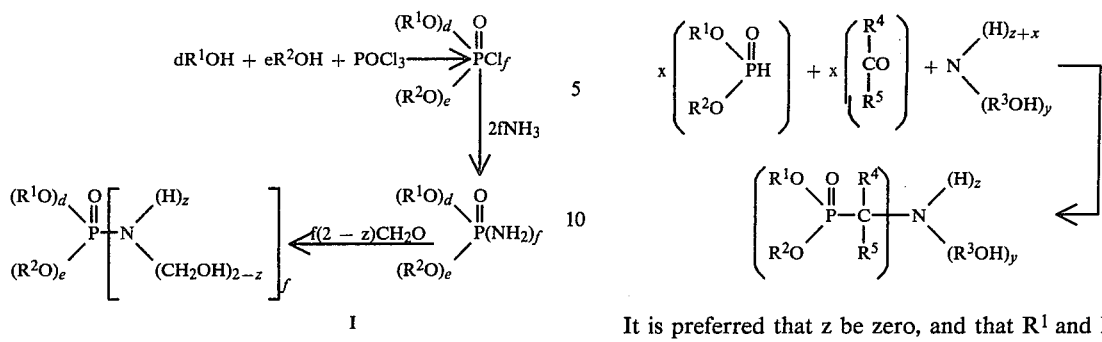

I

Some of the preferred phosphorus compounds which are described by formula I and can be utilized in the intumescent composition of this invention are, e.g., diethyl-N,N-dimethylol phosphoramidate, trichloroneopentyl-chloroethyl-N,N-dimethylol phosphoramidate, dimethyl-N,N-dimethylol phosphoramidate, methyl ethyl-N,N-dimethylol phosphoramidate, hexyl ethyl-N,N-dimethylol phosphoramidate, tribromoneopentyl methyl-N,N-dimethylol phosphoramidate, propylpentyl-N-methylol phosphoramidate, diethyl-N-methylol phosphoramidate, methyl propyl-N,N-dimethylol phosphoramidate, ethyl propyl-N-methylol phosphoramidate, dibutyl-N,N-dimethylol phosphoramidate, pentyl butyl-N,N-dimethylol phosphoramidate, dipropyl-N,N-dimethylol phosphoramidate, bis-(2-bromoethyl)-N,N-dimethylol phosphoramidate, chloroethyl-chloroneopentyl-N,N-dimethylol phosphoramidate, bis-(2-chloroethyl)-N,N-dimethylol phosphoramidate, bis-(2,3-dibromopropyl)N,N-dimethylol phosphoramidate, and the like. Mixtures of these compounds also may be utilized.

Other phosphorus compounds described by formula I which can be utilized in the intumescent composition of this invention include, e.g., hexamethylol phosphorotriamide, chloroneopentyl-N,N,N',N'-tetramethylol phosphorodiamidate, chloroethyl-N,N'-dimethylol phosphorodiamidate, bis(N,N-dimethylol) phosphorodiamidate, propyl bis(N,N-dimethylol) phosphorodiamidate, and the like. Mixtures of these compounds also may be used.

The phosphorus compound described by formula II may be prepared by conventional methods well known to the art. Thus, the following reaction scheme may be used:

It is preferred that z be zero, and that $R^1$ and $R^2$ be independently selected from the group consisting of alkyl radicals containing from about 1 to about 4 carbon atoms and haloalkyl radicals containing from about 2 to about 4 carbon atoms, that $R^3$ be alkyl of from 1 to about 4 carbon atoms, and that $R^4$ and $R^5$ be hydrogen. In a more preferred embodiment, x is 1, y is 2, and $R^1$ and $R^2$ are independently selected from the group consisting of ethyl and haloethyl.

When $R^1$ and $R^2$ is haloalkyl, the halogen substituent(s) is selected from the group consisting of bromine, chlorine, or mixtures thereof.

Some of the phosphorus compounds which are described by formula II and which can be utilized in the intumescent composition of this invention include, e.g., the phosphorus compounds described in Table I. Mixtures of these compounds also may be utilized. Other comparable compounds will readily suggest themselves to those skilled in the art for use in the intumescent composition of this invention; they are also intended to be comprehended within the scope of this invention.

TABLE I

| $R_1$ | $R_2$ | $R_3$ | $R_4$ | $R_5$ | X | Y | Z |
|---|---|---|---|---|---|---|---|
| ethyl | ethyl | ethylene | H | H | 1 | 2 | 0 |
| chloroethyl | chloroethyl | ethylene | H | H | 1 | 2 | 0 |
| methyl | methyl | propylene | H | H | 1 | 2 | 0 |
| ethyl | butyl | ethylene | H | H | 1 | 2 | 0 |
| chloroisopropyl | chloroisopropyl | propylene | H | H | 1 | 2 | 0 |
| bromoethyl | bromomethyl | ethylene | H | H | 1 | 2 | 0 |
| bromopropyl | bromopropyl | propylene | H | H | 2 | 1 | 0 |
| ethyl | ethyl | ethylene | methyl | methyl | 1 | 2 | 0 |
| chloroethyl | chloroethyl | propylene | chloromethyl | chloromethyl | 1 | 2 | 0 |
| ethyl | ethyl | chloroisopropylene | H | H | 1 | 1 | 1 |
| tribromoneopentyl | chloroethyl | ethylene | H | H | 1 | 2 | 0 |
| ethyl | ethyl | ethylene | H | H | 1 | 1 | 1 |

The intumescent composition of this invention contains an organo-phosphorus acid. It is preferred that said composition contain from about 10 to about 35 percent (by weight) of said acid; it is more preferred that said composition contain from about 14 to about 28 percent (by weight) of said acid. The acid used in the intumescent composition of this invention is selected from the group consisting of:

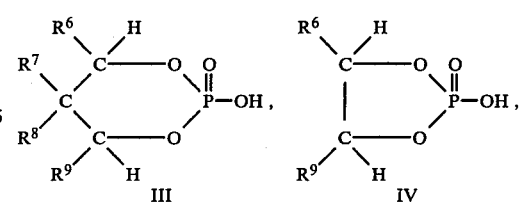

III  IV

-continued

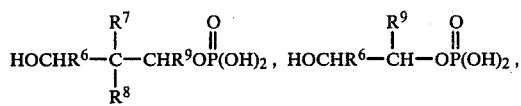

V    VI

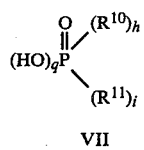

VII and mixtures thereof, wherein $R^6$, $R^7$, $R^8$ and $R^9$ are independently selected from the group consisting of hydrogen, alkyl of from about 1 to about 3 carbon atoms, haloalkyl of from about 1 to about 3 carbon atoms, and hydroxyalkyl of from 1 to about 3 carbon atoms, provided that the total number of carbon atoms in the $R^6$, $R^7$, $R^8$, and $R^9$ groups does not exceed about 5; wherein q is an integer of from 1 to 2, h and i are integers independently selected from the group consisting of 0, 1, and 2, and q plus h plus i equals 3; and wherein $R^{10}$ and $R^{11}$ are independently selected from the group consisting of alkyl of from about 1 to about 6 carbon atoms, haloalkyl of from about 1 to about 6 carbon atoms and from 1 to about 3 halogen atoms, hydroxy-polyalkyleneoxy containing 2 to 6 carbon atoms and 2 to 6 oxygen atoms, alkoxy of from about 1 to about 6 carbon atoms, hydroxyalkoxy of from about 2 to about 6 carbon atoms, haloalkoxy of from about 2 to about 6 carbon atoms and from about 1 to about 3 halogen atoms,

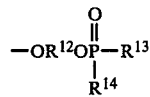

wherein $R^{12}$ is selected from the group consisting of alkylene of from about 2 to about 6 carbon atoms, haloalkylene of from about 3 to about 6 carbon atoms and from about 1 to about 3 halogen atoms, polyalkyleneoxy containing 2 to 6 carbon atoms and 1 to 5 oxygen atoms, and hydroxyalkylene of from 3 to about 6 carbon atoms and 1 to 4 hydroxyls, and $R^{13}$ and $R^{14}$ are independently selected from the group consisting of hydrogen, hydroxyl, alkyl of from about 1 to about 6 carbon atoms, haloalkyl of from about 1 to about 6 carbon atoms and from about 1 to about 3 halogen atoms, hydroxy-polyalkyleneoxy containing about 2 to about 6 carbon atoms and 2 to 6 oxygen atoms, alkoxy of from about 1 to about 6 carbon atoms, hydroxyalkoxy of from about 2 to about 6 carbon atoms, and haloalkoxy of from about 2 to about 6 carbon atoms and 1 to about 3 halogen atoms, provided that the total number of carbon atoms in the $R^{10}$ and $R^{11}$ groups does not exceed about 8.

Some of the acids described by formulae III and IV include, e.g., 2-hydroxy-2-oxo-1,3,2-dioxaphosphorinane, 2-hydroxy-1,3,2-dioxaphospholane-2-oxide, 2-hydroxy-5-methyl-2-oxo-1,3,2-dioxaphosphorinane, 2-hydroxy-4-methyl-1,3,2-dioxaphospholane-2-oxide, 2-hydroxy-4-methyl-2-oxo-1,3,2-dioxaphosphorinane, 2-hydroxy-5-ethyl-2-oxo-1,3,2-dioxaphosphorinane, 2-hydroxy-4-ethyl-1,3,2-dioxaphosphospholane-2-oxide, 2-hydroxy-4-ethyl-2-oxo-1,3,2-dioxaphosphorinane, 2-hydroxy-5-n-propyl-2-oxo-1,3,2-dioxaphosphorinane, 2-hydroxy-4-n-propyl-1,3,2-dioxaphospholane-2-oxide, 2-hydroxy-4-n-propyl-2-oxo-1,3,2-dioxaphosphorinane, 2-hydroxy-5-isopropyl-2-oxo-1,3,2-dioxaphosphorinane, 2-hydroxy-4-isopropyl-4-methyl-1,3,2-dioxaphospholane-2-oxide, 2-hydroxy-4-isopropyl-2-oxo-1,3,2-dioxaphosphorinane, 2-hydroxy-5-chloroethyl-2-oxo-1,3,2-dioxaphosphorinane, 2-hydroxy-4-chloroethyl-1,3,2-dioxaphospholane-2-oxide, 2-hydroxy-4-chloroethyl-2-oxo-1,3,2-dioxaphosphorinane, 2-hydroxy-5-bromomethyl-2-oxo-1,3,2-dioxaphosphorinane, 2-hydroxy-4-bromoethyl-1,3,2-dioxaphospholane-2-oxide, 2-hydroxy-4-bromoethyl-2-oxo-1,3,2-dioxaphosphorine, 2-hydroxy-5-chloropropyl-2-oxo-1,3,2-dioxaphosphorinane, 2-hydroxy-4-chloropropyl-1,3,2-dioxaphospholane-2-oxide, 2-hydroxy-4-chloropropyl-2-oxo-1,3,2-dioxaphosphorinane, 2-hydroxy-5-bromopropyl-2-oxo-1,3,2-dioxaphosphorinane, 2-hydroxy-4-bromopropyl-1,3,2-dioxaphospholane-2-oxide, 2-hydroxy-4-bromopropyl-2-oxo-1,3,2-dioxaphosphorinae, 2-hydroxy-5,5-dimethyl-2-oxo-1,3,2-dioxaphosphorinane, 2-hydroxy-4,5-dimethyl-2-oxo-1,3,2-dioxaphospholane-2-oxide, 2-hydroxy-5,5-bis(bromomethyl)-2-oxo-1,3,2-dioxaphosphorinane, and the like.

Difunctional compounds of formulae V and VI may be utilized in the intumescent composition of this invention. These compounds usually contain both acid and hydroxy substituents. They may be used to replace either the acid compound and/or the phosphorus compound. Some of the difunctional compounds which may be utilized in the composition of this invention include, e.g., 2-hydroxyethyl phosphoric acid, 3-hydroxy-2-propyl phosphoric acid, 1-hydroxy-2-butyl phosphoric acid, 3-hydroxy-2,2-diethyl-1-propyl phosphoric acid, 2,2-dimethyl-3-hydroxy-1-propyl phosphoric acid, 3-hydroxy-1-propyl phosphoric acid, 2,2-bis(bromomethyl)-3-hydroxy-1-propyl phosphoric acid, 2,2-bis(chloromethyl)-3-hydroxy-1-propyl phosphoric acid, 2,2-bis(chloroethyl)-3-hydroxy-1-propyl phosphoric acid, 2,2-bis(hydroxymethyl)-3-bromo-1-propyl phosphoric acid, 2,2-bis(hydroxymethyl)-3-chloro-1-propyl phosphoric acid, and the like.

Some of the acids described by formula VII are shown in Table II.

TABLE II

| $R_{10}$ | $R_{11}$ | g | h | i |
|---|---|---|---|---|
| chloromethyl | | 2 | 1 | 0 |
| 2'-hydroxyethoxyethyl | | 2 | 1 | 0 |
| 2'-hydroxyethoxyethyl | | 1 | 2 | 0 |
| 2,2,2 tris-hydroxy methyl ethyl | | 2 | 1 | 0 |
| 4-hydroxy-1-butyl | | 2 | 1 | 0 |
| chloroethoxy | | 2 | 1 | 0 |
| chloroethoxy | | 1 | 2 | 0 |
| bromoethoxy | | 2 | 1 | 0 |
| bromoethoxy | | 1 | 2 | 0 |
| 1,3 dichloro-2-propoxy | | 2 | 1 | 0 |

TABLE II-continued

| $R_{10}$ | $R_{11}$ | g | h | i |
|---|---|---|---|---|
| 1,3 dichloro-2-propoxy | | 1 | 2 | 0 |
| $-OCH_2CH_2OCH_2CH_2O\overset{O}{\underset{\|}{P}}(OH)_2$ | | 2 | 1 | 0 |
| $-OCH_2CH_2O\overset{O}{\underset{\|}{P}}(OH)_2$ | | 2 | 1 | 0 |
| $-CH_2\underset{CH_2Cl}{\overset{CH_2Cl}{C}}CH_2O\overset{O}{\underset{\|}{P}}(OH)_2$ | | 2 | 1 | 0 |
| $-OCH_2\underset{CH_2OH}{\overset{CH_2OH}{C}}CH_2O\overset{O}{\underset{\|}{P}}(OH)_2$ | | 2 | 1 | 0 |
| methyl | | 2 | 1 | 0 |
| methyl | | 1 | 2 | 0 |
| ethoxy | | 2 | 1 | 0 |
| ethoxy | | 1 | 2 | 0 |
| hydroxy polyethyleneoxy (1–3 repeat units) | | 1 | 2 | 0 |
| hydroxy polyethyleneoxy (1–3 repeat units) | | 2 | 1 | 0 |
| chloroethyl | | 2 | 1 | 0 |
| chloroethyl | | 1 | 2 | 0 |
| tribromoneopentoxy | | 2 | 1 | 0 |
| trichloroneopentoxy | | 2 | 1 | 0 |
| chloroneopentoxy | | 2 | 1 | 0 |
| butyl | | 2 | 1 | 0 |
| butyl | | 1 | 2 | 0 |
| butoxy | | 2 | 1 | 0 |
| butoxy | | 1 | 2 | 0 |
| $-OCH_2CH_2O\overset{O}{\underset{\|}{P}}(OCH_2CH_2OCH_2CH_2OH)_2$ | | 2 | 1 | 0 |
| ethyl | butyl | 1 | 1 | 1 |
| ethoxy | butoxy | 1 | 1 | 1 |
| chloroethoxy | 1,3-dichloro-2-propoxy | 1 | 1 | 1 |
| chloroneopentoxy | chloroethoxy | 1 | 1 | 1 |
| chloromethyl | chloroethoxy | 1 | 1 | 1 |
| bromopropoxy | chloroethoxy | 1 | 1 | 1 |

Compounds III and V may be prepared by hydrolyzing an acid chloride of III in accordance with the following reaction scheme:

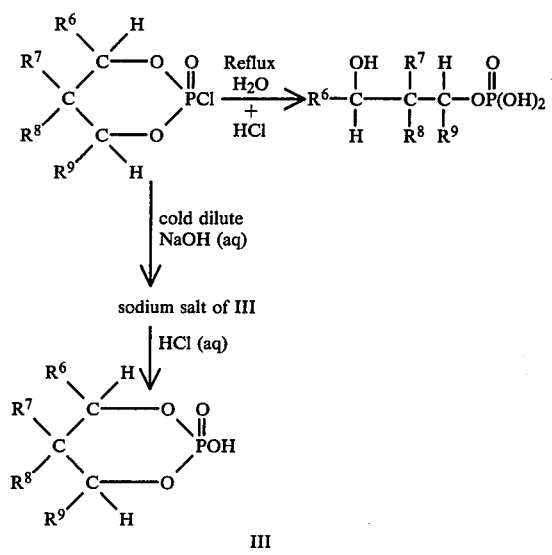

A comparable reaction scheme utilizing the acid chloride of structure IV as the reactant may be used to prepare compounds IV and VI.

Many of the acids described by formula VII may be prepared by hydrolyzing the acid chloride of compound VII. The acid chloride starting materials are well known to the art. When the acids are prepared by this method, the initial hydrolysis reaction may be conducted in water under mild conditions and/or in the presence of sufficient caustic so that the pH of the reaction mixtures is at least 7.0. Hydrochloric acid may be used to neutralize the sodium salt of the acid and help release the free acid. The following reaction scheme may be used to prepare this compound.

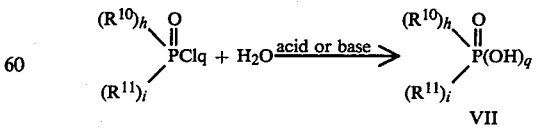

It is preferred that the acid used in the intumescent composition of this invention be soluble in either water and/or the phosphorous compound used in this composition; when one part of the preferred acid is mixed with no more than one part of the component in which it is soluble at 25 degrees centigrade, a one phase solution is formed.

The intumescent composition of this invention contains water. It is preferred that said composition contain from about 5 to 50 percent (by weight) of water. It is more preferred that said composition contain from about 8 to about 40 percent (by weight) of water.

The intumescent composition of this invention may be prepared by means known to the art. One may, e.g., mix in a dry state the cyclic nitrogen compound, the phosphorus compound, and the acid and then add the specified amount of water to the mixture. It is preferred, however, to mix solutions of said compounds together; the concentrations of such solution are such that, after they are mixed together, the intumescent composition which results contains the specified amounts of water, cyclic nitrogen compound, phosphorus compound, and acid.

Generally, the components of the intumescent composition of this invention are mixed together for at least about 60 seconds, although longer and shorter mixing times may be used.

The intumescent composition of this invention should be applied to a wood substrate within about 240 minutes of the time it is prepared. Although it is useful for most wood substrates, it is especially useful for imparting durable flame retardancy to a plywood substrate.

Plywood is a material made by bonding wood together with an adhesive. The layers are usually veneer; they are generally no greater than about 0.1875" thick for hardwood plywood and 0.1667" thick for softwood plywood. The successive layers (plies) have their grains at a definite angle to each other, usually 90 degrees.

The composition of this invention may be advantageously utilized with any of the plywood substrates well known to the art. It may be applied to this type of substrate by any method known to the art such as, e.g., by spraying, brushing, or coating the composition onto the plywood. It is preferred that the dry solids add on of the intumescent composition of this invention be from about 3 to about 15 grams per square foot of plywood surface treated. The "add on" is determined by weighing the plywood substrate before and immediately after it is treated. The percent of the solids in the composition applied times this difference is the number of grams of dry solids applied; the number of grams of dry solids applied divided by the number of square feet treated in the "add on" referred to in this specification. One coat of the intumescent composition of this invention may be applied; it is preferred, however, to apply two or more coats.

After the composition of this invention is applied to the wood substrate, it is dried. It may be air dried, in which case up to about 30 hours should be allowed for it to dry. It may be dried by techniques well known to those skilled in the art. If heat is applied to the treated substrate, it is preferred to use a temperature of from about 70 to about 170 degrees centigrade for from about 18 seconds to about 20 minutes. It is more preferred to dry the treated substrate at a temperature of from about 95 to about 110 degrees Centigrade for from about 1 to about 10 minutes.

The composition of this invention also is useful for imparting flame retardance to flammable substrates other than wood paneling. Such substrates include, but are not limited to, those comprised of fibers such as cellulosics, of fibers of synthetic organic polymers such as polyesters and of combinations of these types of fiber and of reconstituted wood products such as fiberboard and particle board. The inventive composition is particularly useful for imparting flame retardance to flammable fibrous substrates used to filter out solids or particulates from fluid streams, either liquid or gaseous. Treatment of filter media with flame retardant systems which rely for their efficacy on the presence of halogen and a metallic oxide such as antimony oxide has been found to give the undesirable effect of reducing fluid flow through the filter. However, treatment of filter media, particularly filter paper, with the inventive composition gives fire retardance without deleterious effects on flow-through rate. Flame retardant filters are especially desirable in fields of use such as automotive carburetor air filters and fuel filters where high temperature and/or flammable fuels are present.

The composition can be used to afford protection from fire damage of non-flammable substrates such as metal, glass or concrete.

The inventive composition is useful also as an adhesive or binder and can be used to replace part, or all, of the adhesive used, for example, to laminate plies of wood together to form plywood panels, to bind together the wood particles used in hardboard, chipboard, particle board and the like, to give structural integrity to non-woven forms, fabrics or batts made from organic fibers such as polyesters or from inorganic fibers made from glass or minerals. The flame retarding effect of the inventive compositions aids in preventing fire damage to articles in which they are used as adhesives or binders.

Whether the inventive composition is used solely as flame retarding additive or as a combination fire-retardant/adhesive, it can be applied as a surface treatment or as an impregnation by art-known methods such as spraying, brushing, padding, rolling, dipping, etc. The weight percentage of the inventive composition in the formulation actually applied to the substrate can be adjusted to give desired results in regard to factors such as weight pickup per application or viscosity of the formulation. Additional water may be added to achieve variation of viscosity or to control pickup. In some instances, such as in treating paper, where excessive exposure to water may not be desired, an organic solvent can be used. Suitable organics include the lower alcohol such as methanol, ethanol, butanol and the like—and lower molecular weight glycol ethers. The amount of the inventive composition in the final formulation can be from about 1 weight percent to 100 weight percent.

The amount of weight pickup can also be controlled by varying the quantity of formulation removed from the substrate by operations such as passing the treated or impregnated substrate through rolls under pressure.

After application of the inventive composition to the desired substrate, the final commercial product is produced by a removal of the volatiles—water or organic diluent-followed by a "curing" or polymerization of the dry solids into a water-resistant coating. It is to be understood that this curing occurs even in the presence of the volatiles and even at room temperture, however the rate at which it occurs is increased by higher temperatures. Further, it is often desirable to first remove volatiles in order to have a more easily handleable article. The volatiles-removal and curing can be done in one operation or can be done in two stages: a lower temperature treatment for volatiles-removal followed by a higher temperature for curing. For substrates other than the plywood substrates hereinabove described, the volatiles removal can be accomplished by air drying at room temperature for a period of from 16 to 48 hours however it is preferable to use temperatures of from about 70° C.–110° C. for a period of from about 0.2 to 20 minutes. It is preferred to carry out the curing operation at temperatures of from about 110° C. to 250° C. for periods of from about 0.2 to 10 minutes.

Where the type of substrate to which the inventive composition is applied is essentially nonporous, so that substantially all of the inventive composition is on its surface, the "add on" is calculated in terms of weight per area as described hereinabove. For such substrates, it is preferred that the add on be from about 3 grams to about 18 grams per square foot.

Where the type of substrate which the inventive composition is applied is porous enough to allow a substantial amount of the inventive composition to penetrate into its interior, substrates, for example, such as papers, fabric (woven and non-woven) and batts, dry solids add on can better be expressed as a weight percentage calculated by use of the expression:

$$\frac{\text{(Weight Substrate + Dry Solids) Minus (Weight Untreated Substrate)}}{\text{(Weight Untreated Substrate)}} \times 100$$

The weight of the substrate+dry solids is conveniently found by weighing the treated substrate after removal of volatiles. The weight of dry solids can also be found, as described hereinabove, by finding the difference in weight of the substrate before and immediately after it is treated and then multiplying this difference by the percentage of the solids in the inventive composition applied. Where, in this specification, dry solids add on is given as a percentage, it has been calculated by use of the above expression. For substrates where this type of dry solids add on calculation is used, it is preferred that the dry solids add on be from about 1% to about 100%. A more preferred range of the dry solids add on is from about 5% to 100%.

In the specific uses of the inventive composition as the total adhesive or as a component of adhesives, for plywood, particle board, and the like, no changes in the usual practices of industry regarding the time, temperature and pressure used to effect bonding are required.

As an adhesive, a preferred range of dry solids add on of the inventive composition is from about 3 to 18 grams per square foot of glued surface or from about 3% to 100%.

The following examples illustrate the claimed invention and are not to be deemed limitative thereof. Unless otherwise specified, all parts are by weight, all temperatures are in degrees Centigrade, all weights are expressed in grams, and all volumes are expressed in milliliters.

EXAMPLE 1

N,N-dimethylol-bis(chloroethyl)phosphoramidate

Thirteen hundred and forty-six grams (4.99 moles) of tris (chloroethyl phosphite) were charged to a three-liter flask equipped with a stirrer and a gas delivery tube. This reactant was cooled with an ice bath to a temperature of less than 20 degrees centigrade; and the addition of chlorine to the tris (chloroethyl phosphite) was commenced. The rate of chlorine addition was maintained so that the temperature of the reaction mixture did not rise above 25 degrees centigrade; chlorine was added to the reaction mixture over a period of 240 minutes until the chlorination reaction was complete (as was indicated by the reaction mixture turning to a yellow color). Dichloroethane by-product was removed from the reaction mixture by reduced pressure distillation. The reaction mixture was then maintained at ambient temperature and allowed to stand overnight.

Ammonia was added to the reaction mixture over a period of about 210 minutes; during the ammonia addition, chloroform was added to maintain the reaction mixture in a fluid state, and the reaction mixture was cooled so that the temperature of the reaction mixture did not exceed about 30 degrees centigrade. The reaction was continued until the ammonia had replaced all of the chlorine which was bonded directly to the phosphorus atom; the reaction was conducted over a period of 210 minutes.

Bis(chloroethyl)phosphoramidate was washed with water and filtered. A white solid with a melting point of 68 degrees centrigrade was obtained; it contained 21.69 percent carbon, 4.66 percent hydrogen, 30.6 percent chlorine, 6.05 percent nitrogen, and 13.57 percent phosphorus.

N,N-dimethylol-bis(chloroethyl) phosphoramidate was prepared by dissolving bis(chloroethyl) phosphoramidate in a 37 percent aqueous solution of formaldehyde; about 2.1 moles of formaldehyde per mole of phosphoramidate were present in the reaction mixture. The pH of the reaction mixture was maintained at about 10 during the addition of the formaldehyde to the phosphoramidate; after these reactants formed a solution, however, the pH of the reaction mixture was adjusted to about 7 via the addition of dilute hydrochloric acid to the reaction mixture. The product obtained was dried and subjected to $H^1$ and $P^{31}$ N.M.R. analyses; the spectra obtained were substantially in accordance with those expected from the proposed structure.

EXAMPLE 2

2,2-bis(bromomethyl)-3-hydroxy-1-propyl phosphoric acid

Five thousand two hundred and forty grams (20.0 moles) of dibromoneopentyl glycol and 3,070 grams of phosphoryl chloride were placed in a 12-liter round bottom flask equipped with a stirrer, heating mantle and condenser. The reaction mixture was consecutively maintained at ambient temperature for 30 minutes, a temperature of 40–45 degrees centigrade for 60 minutes, a temperature of 50 degrees centigrade for 60 minutes, a temperature of 70 degrees centigrade for 60 minutes, a temperature of 90 degrees centigrade for 120 minutes, and a temperature of 110 degrees centrigrade (under aspirator vacuum) for 60 minutes. The reaction mixture was allowed to stand overnight. The reaction mixture thus formed was subjected to an absolute pressure of about 25 millimeters of mercury for about 360 minutes during which water and hydrogen chloride were removed from the mixture and the reaction temperature was allowed to increase to a maximum temperature of about 100 degrees centigrade.

The phosphoric acid obtained was a semi-solid material. The product was dissolved in sufficient water to produce a 60 percent solution. Elemental analysis indicated that it contained 27.0 percent of bromine; according to theory, it should have contained 28.5 percent of bromine.

EXAMPLE 3

Fifty parts of an 80 percent aqueous solution of Aerotex Resin M-3 ®, a methylated trimethylol melamine compound available from the American Cyanamide Corporation, were mixed with 25 parts of a 60 percent aqueous solution of N,N-dimethylol-bis(chloroethyl) phosphoramidate and 25 parts of a 60 percent aqueous solution of 2,2-bis(bromomethyl)-3-hydroxyl-1-propyl phosphoric acid; the former compound was prepared in substantial accordance with the procedure described in Example 1, and the latter compound was prepared in substantial accordance with the procedure described in Example 2.

Two coats of this formulation were brushed onto a lauan plywood sample (which was 24.0" long, 3.5" wide, and 0.1875" thick) to a dry solids add on of 8 grams per square foot. The coated sample was then dried at a temperature of about 100 degrees centigrade for about 5 minutes. Thereafter the sample was subjected to a two-foot tunnel test to determine the flame spread rate; this test was conducted in substantial accordance with the procedure descried in an article entitled "Two-Foot Tunnel Test", Journal of Paint Technology, Vol. 11, No. 565, February 1972, pp 43–47; however the panels were not aged as described in this article.

The two-foot tunnel test is similar to the UL Steiner 25-foot tunnel test described by ASTM E84-68. In the former test, the two-foot tunnel was inclined 28 degrees from the horizontal and utilized approximately 96 square inches of test surface. The test specimen was mounted on an angle iron frame in such a way that the surface to be evaluated formed the ceiling of the tunnel. A standard Meeker burner was placed at the lower end of the tunnel, and the specimen was subjected to the flame from this burner for five minutes; during the first four minutes, the length of the advance of the flame front up the inclined panel was recorded at 15 second intervals. The flame lengths were measured by observing the flame front advance through a calibrated window located on the side of the tunnel. The tunnel was calibrated prior to specimen testing by determining the difference in flame lengths of a specimen of asbestos cement board and a specimen of red oak; this difference, by introduction of a constant K, was given a flame spread rating ("FSR") of 100. The flame spread rate calculation was made in accordance with the formula $F.S.R. = (L_n - L_a)K$ wherein F.S.R. was the flame spread rating, $L_n$ was the observed flame of the specimen tested, $L_a$ was the flame for asbestos cement board, $L_o$ was the observed flame length for the red oak sample, and $$K = \frac{100}{L_o - L_a}.$$

The samples were weighed both before and after being treated in the two-foot tunnel, and the percent weight loss due to combustion of the sample was determined.

The coated plywood sample of this example had a flame spread rating of 20 and lost about 6 percent of its weight after the two foot tunnel test. The coating intumesced during the test and protected the wood surface.

A control experiment was conducted wherein the lauan plywood sample which was subjected to the two foot tunnel test was not coated with the intumescent composition of this invention. The uncoated plywood sample had a flame spread rating of 95 and lost about 18 percent of its weight after the two foot tunnel test.

EXAMPLES 4–16

In substantial accordance with the procedure described in Example 3, various coating formulations were prepared, applied to lauan plywood samples measuring 24"×3.5"×0.1875", and dried; and the coated plywood samples were tested in the two foot tunnel to determine their flame spread ratings and how much weight they lost during this test. Table III presents the results of these experiments, indicating the formulations and conditions used in each Example.

TABLE III

| Example Number | 4 | 5 | 6 | 7 | 8 | 9 | 10 | 11 | 12 | 13 | 14 | 15* | 16* |
|---|---|---|---|---|---|---|---|---|---|---|---|---|---|
| Parts of 80 percent aqueous solution of methylated trimethylol melamine | 40 | 40 | 40 | 60 | 70 | 0 | 50 | 50 | 0 | 0 | 50 | 50 | 50 |
| Parts of methylated hexamethylol melamine | 0 | 0 | 0 | 0 | 0 | 50 | 0 | 0 | 40 | 50 | 0 | 0 | 0 |
| Parts of 60 percent aqueous solution of N,N-dimethylol-bis(chloroethyl)phosphoramidate | 30 | 40 | 20 | 20 | 15 | 0 | 0 | 0 | 0 | 0 | 0 | 0 | 0 |
| Parts of 60 percent aqueous solution of 2,2-bis(bromomethyl)-3-hydroxy-1-propyl phosphoric acid | 30 | 20 | 40 | 20 | 15 | 25 | 7 | 25 | 25 | 25 | 25 | 0 | 0 |
| Parts of diethyl-N,N-bis(2-hydroxyethyl)amino methane phosphonate | 0 | 0 | 0 | 0 | 0 | 25 | 25 | 25 | 25 | 25 | 25 | 25 | 25 |
| Parts of water | 0 | 0 | 0 | 0 | 0 | 0 | 13 | 0 | 10 | 0 | 0 | 10 | 0 |
| Dry solids add on (Grams/square foot) | 7 | 8 | 8 | 6 | 5 | 7 | 8 | 8 | 7 | 7 | 8 | 12 | 8 |
| Weight loss, percent | 6 | 6 | 5 | 6 | 6 | 5 | ND | 5 | 5 | 5 | 5 | 6 | 6 |
| Flame spread rating | 20 | 20 | 20 | 20 | 30 | 20 | 35 | 20 | 30 | 30 | 30 | 35 | 30 |

*Formulation also contained 15 parts of dibutyl hydrogen phosphate
**Formulation also contained 25 parts of a 60 percent aqueous solution of mono-(tribromoneopentyl) phosphoric acid

EXAMPLES 17–18

In substantial accordance with the procedure described in Example 3, a coating formulation containing 50 parts of a 80 percent aqueous solution of methylated trimethylol melamine, 25 parts of a 60 percent aqueous solution of N,N-dimethylol-bis(chloroethyl)phosphoramidate, and 25 parts of a 60 percent aqueous solution of 2,2,-bis(bromomethyl)-3-hydroxy-1-propyl phosphoric acid was prepared, coated onto a lauan plywood sample measuring 24.0"×3.5"×0.1875" to a dry solids add on of 7 grams per square foot, dried, and tested to determine how much smoke and carbon monoxide the coated plywood sample generated during pyrolysis.

In accordance with National Fire Protection Association Test number 258, the coated plywood sample was tested under non-flaming conditions in the NBS Smoke Chamber. This test is described in an article by D. Gross, J. Loftus, and A. F. Robertson entitled "Method for Measuring Smoke from Burning Materials", *Symposium on Fire Test Methods—Restraint & Smoke,* 1966, ASTM STP 422, Am. Soc. Testing Mats., 1967, p. 166; this article is hereby incorporated by reference into this specification.

Both a plywood sample coated with the formulation of this Example and an uncoated control sample of the lauan plywood sample were tested. The maximum smoke density ("Dmc") generated by the plywood sample and the time to reach "Dmc" in minutes during the test was determined, as was the weight loss of the plywood sample (percent weight loss). The maximum smoke density was corrected for smoke deposited on the optical windows. Air samples were continually removed from the chamber at the rate of 0.5 liter/minute. The amount of carbon monoxide present in these samples was determined (and was expressed as "CO conc., ppm"). The results of these experiments are shown in Table IV.

TABLE IV

| Example Number | Coating Description | Dmc | Percent Weight Loss | Time to 2 Dmc (Minutes) | CO Conc.(p.p.m.) 5 min. | 10 min. | 20 min. |
|---|---|---|---|---|---|---|---|
| 17 | None | 324 | 82 | 9.5 | 420 | 1600 | 3880 |
| 18 | Coating of Example 3 | 152 | 36 | 20. | 60 | 190 | 570 |

EXAMPLE 19

A coating formulation containing 50 parts of an 80 percent aqueous solution of methylated trimethylol melamine, 25 parts of a 60 percent aqueous solution of 2,2-bis(bromomethyl)-3-hydroxy-1-propyl phosphoric acid, and 25 parts of "Fyrol 6" (a commercial flame retardant available from the Stauffer Chemical Corporation which contains diethyl-N,N-bis(2-hydroxyethyl)amino methane phosphonate) was prepared. In substantial accordance with the procedures described in Examples 3 and 20–21, this coating was applied to a lauan plywood sample measuring 24.0"×3.5"×0.1875" to a dry solids add on of 7 grams per square foot, dried, and tested in the NBS chamber to determine how much smoke and carbon monoxide the coated plywood sample generated during pyrolysis.

The maximum smoke density of the coated sample of this Example was 180; the time to Dmc was 20 minutes; and the sample lost 41 percent of its weight during the test. The carbon monoxide concentrations in the air samples at 5 minutes, 10 minutes, and 20 minutes after the test began were 60, 200, and 670 parts per million, respectively.

EXAMPLE 20

A coating formulation containing 50 parts of an 80 percent aqueous solution of methylated hexamethylol melamine (available as "Resimene 745"® from the Monsanto Chemical Corporation), 25 parts of a 60 percent aqueous solution of 2,2-bis(bromomethyl)-3-hydroxy-1-propyl phosphoric acid and 25 parts of diethyl-N,N-bis(2-hydroxyethyl)amino methane phosphonate was prepared. In substantial accordance with the procedures described in Examples 3 and 17–19, this coating was applied to a lauan plywood sample measuring 24.0"×3.5"×0.1875" to a dry solids add on of 7 grams per square foot, dried, and tested in the NBS chamber to determine how much smoke and carbon monoxide the coated plywood sample generated.

The maximum smoke density of the coated sample of this Example was 130. The time to "Dmc" was 20 minutes, and the sample lost 32 percent of its weight during the test. The carbon monoxide concentrations in the air samples at 5 minutes, 10 minutes, and 20 minutes after the test began were 40, 130, and 430 parts per million, respectively.

EXAMPLE 21

Fifty parts of an 80 percent aqueous solution of methylated trimethylol melamine were mixed with 25 parts of a 60 percent aqueous solution of pentaerythritol disphosphoric acid and 25 parts of diethyl-N,N-bis(2-hydroxyethyl)amino methane phosphonate; in accordance with the procedure described in Example 3, the coating formulation so obtained was applied to a lauan plywood sample measuring 24.0"×3.5"×0.1875" to a dry solids add on of 10 grams per square foot and dried; and the coated plywood sample was then tested in the two-foot tunnel test.

The coated plywood sample of this Example had a flame spread rating of 30 and lost about 6 percent of its weight during the two foot tunnel test.

EXAMPLE 22

A coating containing 50 parts of an 80 percent aqueous solution of methylated hexamethylol melamine, 25 parts of diethyl N,N-bis(hydroxyethyl)amino methane phosphonate, and 25 parts of a 60 percent aqueous solution of monotribromoneopentyl phosphoric acid was prepared, applied to a lauan plywood sample measuring 24.0"×3.5"×0.1875" to a dry solids add on of 7 grams per square foot, and dried. The coated plywood sample was subjected to the two foot tunnel test described in Example 3; it had a flame spread rating of 20 and lost 6 percent of its weight during this test.

COMPARATIVE EXAMPLES 23-28

Various compositions which are outside the scope of the claims of this application were evaluated. In each of these examples, the composition described was coated onto a lauan plywood sample measuring 24.0"×3.5"×0.1875" to the dry solids add on indicated, and the coated plywood sample was dried and tested in the two foot tunnel in accordance with the procedure described in Example 3. Table V indicates what occurred in these experiments.

TABLE V

| Example Number | Composition Tested | Dry Solids Add On | Flame Spread Rating | Percent Weight Loss |
|---|---|---|---|---|
| 23 | 50 parts 80% aqueous soln. methylated trimethylol melamine 50 parts 60% aqueous soln. N,N-bismethylol-bis(chloroethyl)phosphoramidate | 8 | 70 | 13 |
| 24 | 50 parts of methylated hexamethylol melamine 48 parts diethyl-N,N-bis(2-hydroxyethyl)amino methane phosphonate 2 parts paratoluene sulfonic acid | 9 | 100 | 12 |
| 25 | 50 parts of methylated hexamethylol melamine 50 parts of diethyl-N,N-bis (2-hydroxyethyl)amino methane phosphonate | 8 | 115 | 14 |
| 26 | 50 parts 80% aqueous soln. methylated trimethylol melamine 25 parts diethyl-N,N-bis (2-hydroxyethyl)amino methane phosphonate 25 parts of the ammonium salt of dibutyl hydrogen phosphate | 7.5 | 70 | 12 |
| 27 | 50 parts 80% aqueous soln. methylated trimethylol melamine 25 parts diethyl-N,N-bis (2-hydroxyethyl)amino methane phosphonate 15 parts neopentyl glycol 10 parts water | 9 | 80 | 10 |
| 28 | 50 parts 80% aqueous soln. methylated trimethylol melamine 25 parts diethyl-N,N-bis (2-hydroxyethyl)amino methane phosphonate 25 parts of Antiblaze 19 ®** | 8 | 80 | N.D. |

*Coating tacky and does not cure well.
**Antiblaze 19 ® is a commercially available phosphorus-containing flame retardant which is sold by the Mobile Chemical Company.

EXAMPLE 29

Fifty parts of an 80 percent aqueous solution of Aerotex Resin M-3 ® were mixed with 25 parts of a 60 percent aqueous solution of N,N-dimethylol-bis(chloroethyl)phosphoramidate and 25 parts of a 60 percent aqueous solution of 2,2-bis(bromomethyl)-3-hydroxy-1-propyl phosphoric acid. Two coats of this formulation were applied to samples of lauan plywood which were 24.0" long×3.5" wide×0.1875" thick to a dry solids add on of 9 grams per square foot; one side of each sample was coated, and the coated samples were then dried at a temperature of about 100 degrees centigrade for about 5 minutes.

One of the samples, the "control", was subjected to the two foot tunnel test described in Example 3 to determine its flame spread rating and the amount of weight it lost during the test. The other sample was subjected to accelerated aging conditions to determine whether the flame retardant properties of the coating of this invention were affected by heat, water, and ultraviolet light. In accordance with A.S.T.M. test G-26-70, the sample was tested in a "Weather-Ometer" (Model 25/18-WR manufactured by the Atlas Electric Device Company of Chicago, Ill.); the sample was maintained at a relative humidity of from about 60 to about 65, and a 120 minute cycle wherein there were 102 minutes of light followed by 18 minutes of light and spray was used. After being subjected to these conditions in the "Weather-Ometer" for 100 hours, the sample was tested in the two foot tunnel to determine its flame spread rating and the amount of weight it lost during the test.

The control sample, which was not subjected to UV exposure, had a flame spread rating of 30 and lost 5 percent of its weight. The sample which had been subjected to 100 hours of exposure conditions had a flame spread rating of 35 and about 5 percent of its weight was lost.

EXAMPLE 30

Fifty parts of an 80 percent aqueous solution of Aerotex Resin M-3 ® were mixed with 25 parts of diethyl-N,N-bis(2-hydroxyethyl)amino methane phosphonate and 25 parts of a 60 percent aqueous solution of 2,2-bis(bromomethyl)-3-hydroxy-1-propyl phosphoric acid. In accordance with the procedure of Example 3, two coats of this formulation were applied to both sides of samples of lauan plywood which were 24.0" long×3.5" wide×0.1875" thick to a dry solids add on of 9 grams per square foot on each side and the coated samples were then dried at a temperature of about 100 degrees centigrade for about 5 minutes.

One of the samples, the "control", was subjected to the two foot tunnel test described in Example 3. In accordance with the procedure described in Example 29, the other sample was subjected to accelerated aging conditions for 18 hours; the relative humidity was maintained at 60–65%, and a 120 minute cycle wherein there were 102 minutes of light followed by 18 minutes of light and spray was used. The sample subjected to these conditions was removed from the "Weather Ometer" after 18 hours and subjected to the two foot tunnel test.

The control sample had a flame spread rating of 30 and lost 5 percent of its weight during the two foot tunnel test. The sample which had been subjected to 18 hours of accelerated aging conditions had a flame spread rating of 30 and lost 5 percent of its weight during the two foot tunnel test.

COMPARATIVE EXAMPLES 31–34

In accordance with the procedures described in Examples 29 and 30, various formulations outside the scope of this invention were tested in the two foot tunnel to determine their flame spread ratings and the percent of weight they lost during the two foot tunnel test. Each formulation was applied to a dry solids add on of 9 grams per square foot to samples of lauan plywood which were 24.0" long×3.5" wide×0.1875" thick; both sides of the lauan plywood samples were coated with the formulations. The coated plywood samples were dried at a temperature of about 100 degrees centigrade for about 5 minutes.

The two-foot tunnel tests were conducted for two plywood samples coated with each formulation—one on a sample which had not been subjected to accelerated aging conditions, and one on a sample which was subjected to the accelerated aging conditions described in Example 32 for 100 hours.

The formulation used in Example 31 contained 50 parts of an 80% aqueous solution of Aerotex Resin- M3 ® and 50 parts of a 60 percent aqueous solution of 2,2-bis(bromomethyl)-3-hydroxy-1-propyl phosphoric acid. The formulation used in Example 32 contained 70 parts of an 80 percent aqueous solution of Aerotex Resin M-3 ®, 15 parts of an 85 percent aqueous solution of phosphoric acid, and 15 parts of water. The formulation used in Example 33 contained 50 parts of Aerotex Resin M-3 ® and 50 parts of diethyl-N,N-bis(2-hydroxyethyl) amino methane phosphonate. No formulation was used in Example 34—the uncoated plywood samples were tested at "time zero" and after 100 hours of accelerated aging.

The results of these experiments are presented in Table VI.

TABLE VI

| | Example No. | | | |
|---|---|---|---|---|
| | 31 | 32 | 33 | 34 |
| Flame Spread Rating, 0 Hours | 50 | 110 | 65 | 95 |
| Flame Spread Rating, 100 Hours | 50 | 110 | 85 | 115 |
| Percent Weight Loss, 0 Hours | 7 | 9 | 8 | 14 |
| Percent Weight Loss, 100 Hours | 7 | 12 | 8 | 15 |

The plywood sample of Example 32 generated black smoke during two foot tunnel tests of both the exposed and unexposed samples.

EXAMPLES 33-36

Other organo-phosphorus acids may be used in the intumescent composition of this invention with equally good results. Various formulations were prepared and tested in accordance with the procedure described in Example 3.

A formulation containing 50 parts of an 80 percent aqueous solution of methylated trimethylol melamine, 25 parts of diethyl-N,N-bis(2-hydroxyethyl)amino methane phosphonate, and 25 parts of 2-hydroxy-5,5-dimethyl-1,3,2-dioxo-phosphorinane, when applied to a dry solids add on of 8 grams per square foot, had a flame spread rating of 30 and lost 5 percent of its weight.

A formulation containing 25 grams of a 60 percent aqueous solution of bis(dichloroisopropyl)phosphoric acid, 25 parts of diethyl-N,N-bis(2-hydroxyethyl)amino methane phosphonate, and 50 parts of an 80 percent aqueous solution of methylated trimethylol melamine, when applied to a dry solids add on of 10 grams per square foot, had a flame spread rating of 30 and a percent weight loss of about 5.5%.

A formulation containing 50 grams of an 80 percent aqueous solution of methylated trimethylol melamine, 25 parts of a 60 percent aqueous solution of bis(2-chloroethyl)phosphoric acid, and 25 parts of diethyl-N,N-bis(2-hydroxyethyl)amino methane phosphonate, when applied to a dry solids add on of 10 grams per square foot, had a flame spread rating of 35 and a percent weight loss of 6.

A formulation containing 10 parts of chloroneopentyl phosphoric acid, 55 parts of an 80 percent aqueous solution of methylated trimethylol melamine, 10 parts of water, and 25 parts of diethyl-N,N-bis(2-hydroxyethyl)amino methane phosphonate, when applied to a dry solids add on of 10 grams per square foot, had a flame spread rating of 35 and a percent weight loss of 6.

EXAMPLES 37-38

Some organo-phosphorous acids outside the scope of the claims of this case were evaluated in intumescent compositions; these acids contained aryl substituents. Various formulations were prepared and tested in accordance with the procedure of Example 3.

Formulations containining 50 parts of an 80 percent aqueous solution of methylated trimethylol melamine, 25 parts of diethyl-N,N-bis(2-hydroxyethyl)amino methane phosphonate, and an aryl-substituted organo-phosphorus acid were prepared. The formulation of Example 37 contained 25 parts of a 60 percent aqueous solution of phenyl phosphonic acid. The formulation of Example 38 contained 25 parts of a 60 percent aqueous solution of phenyl phosphoric acid. Both formulations were applied to an add on of 10 grams per square foot.

The formulation of Example 37 had a flame spread rating of 110 and lost 14 percent of its weight. The formulation of Example 38 had a flame spread rating of 85 and loss 11 percent of its weight.

EXAMPLE 39

A formulation was prepared containing 200 parts of an 80% aqueous solution of Aerotex ® Resin M-3, 100 parts of 2,2-bis(bromomethyl)-3-hydroxy-1-propyl phosphoric acid, 100 parts of Fryol ® 6 and 400 parts of water. Samples of fabric were padded with this formulation, nipped on rolls and then heated at a temperature of approximately 100° Centigrade for a period of approximately 5 minutes. The test pieces were then subjected, while in a vertical position, to the flame of a paper match for a period of 15 seconds. The behavior of the fabric while exposed to flame was noted as to whether "dripping" of the fabric occurred; behavior after flame removed was also noted as to whether the fabric self-extinguished or continued to burn.

Test results are given in Table 7 below.

TABLE 7

| Sample Fabric | Dry Solids Add On | Flame Test |
|---|---|---|
| Polypropylene, Untreated | — | Drips, Burns |
| Polypropylene, Treated | 55% | Drips, Burns |
| Cotton, Untreated | — | Burns |
| Cotton, Treated | 35.1 | No Flame; S.E. |
| Polyester/Cotton, Untreated | — | Drips; Burns |
| Polyester/Cotton, Treated | 26.1 | No Drip; S.E. |
| Polyester, Untreated | — | Drips; Burns |
| Polyester, Treated | 44.1 | No Drips; S.E. |
| Wool, Untreated | — | Burns |
| Wool, Treated | 23.1 | No Drips; S.E. |

Note: S.E. = Self extinguishing.

EXAMPLE 40

Fifty parts of an 80% aqueous solution of Aerotex ® Resin M-3, 25 parts of Fyrol ® 6 and 25 parts of a 60% aqueous solution of 2,2-bis (bromomethyl)-3-hydroxy-1-propyl-phosphoric acid were mixed together. This mixture was applied to a surface of fiberglass-reinforced polyester to give a dry add on of 6 grams per square foot. The treated surface, when held in a vertical position and subjected to the flame of a propane torch for a period of 60 seconds did not ignite. An untreated piece of polyester, tested in the same manner, ignited after 15 seconds of flame exposure.

EXAMPLE 41

Five pieces of thin wood paneling, approximately 9 inches by 9 inches were coated with the formulation of example 40. The five panels were stacked, one atop the other, and subjected to a pressure of about 1000 pounds per square inch at a temperature of about 100° Centigrade for a period of about 8 minutes. Weighing the panels before treatment and after treatment and curing indicated that the adhesive was present at a concentration of 8.6 grams per square foot of glueline. On attempting to separate the panels, failure occurred in the wood substrate rather than the glueline.

EXAMPLE 42

The formulation of example 40 was applied to one surface of a piece of window glass to give a dry solids add on of 12 grams per square foot. The flame of a propane torch was impinged on the treated surface for a period of 60 seconds. The coating intumesced, no deleterious effects were noted on the glass. An untreated piece of glass was subjected to a similar flame exposure, distorted from the heat and cracked as it cooled.

EXAMPLE 43

The formulation of example 40 was applied by an air atomizing spray gun to a fiberboard panel to give a dry solids add on of from 12 to 14 grams per square foot. The board was dried at a temperature of about 225° Fahrenheit for a period of about 1.5 minutes. A bunsen burner was adjusted to give a total flame length of 5 inches with an inner blue cone length of 1.5 inches. The fiberboard was held in a vertical position and the blue cone of the flame was impinged on the treated surface at an angle of 20° for a period of 60 seconds. Upon removing the flame, the treated surface self-extinguished in less than 5 seconds. Testing an untreated fiberboard surface in the same manner resulted in the board burning for more than 5 seconds after flame removal.

EXAMPLE 44

Fifty parts of an 80% aqueous solution of Aerotex ® Resin M-3, 25 parts of a 60% aqueous solution of N,N-dimethylol-bis(chloroethyl) phosphoramidate and 25 parts of a 60% aqueous solution of 2,2-bis(bromomethyl)-3-hydroxy-1-propyl-phosphoric acid were mixed together.

This mixture was applied to one face of a block of polyurethane foam. The coated face of the foam was held in a vertical position and subjected to the flame of a propane torch for a period of 3 minutes. The coating intumesced. Only slight scorching of the polyurethane was noted. Untreated polyurethane foam, when subjected in the same manner to the flame of a propane torch, ignited and burned after a flame exposure of less than 30 seconds.

EXAMPLE 45

To 35 parts of the formulation prepared in example 40 is added 65 parts of methanol. Sheets of paper approximately 6 inches by 6 inches are dried at a temperature of about 300° Fahrenheit for a period of about 10 minutes, weighed, dipped into the methanolic solution, removed, sandwiched between two blotters and the sandwich passed through nip rollers to remove sufficient formulation to obtain a dry solids add on of 25%. The sheets are removed from the sandwich, air dried at room temperature for a period of about 1 hour, then are cured at a temperature of about 300° Fahrenheit for a period of about 15 minutes.

EXAMPLE 46

Glass fiber batting was dipped into the formulation of example 40, excess material removed by nipping through rolls and heated for approximately 3 minutes at a temperature of approximately 100° Centigrade. Dry solids add on was B 50.1% (on weight of fiber). Subjecting untreated glass fiber batting to the flame of a propane torch caused it to shrink away from the flame in approximately 2 seconds. The treated glass fiber, when subjected to the same flame exposure, maintained its integrity for a period of about 30 seconds.

The above examples have been described for the purpose of illustration, not limitation. Many other modifications will suggest themselves to those skilled in the art; they are intended to be comprehende within the scope of the invention.

The embodiments of this invention in which an exclusive property or privilege is claimed are as follows:

1. An intumescent composition containing a cyclic nitrogen compound, a hydroxy-containing organo-phosphorus compound, an organo-phosphorus acid, and water, wherein:

(a) said cyclic nitrogen compound is:

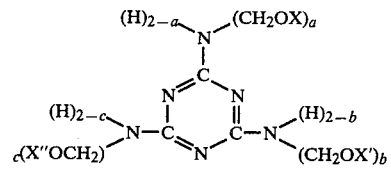

wherein a, b, and c are integers selected from the group consisting of 1 and 2, a plus b plus c equal about 3 to 6, X, X', and X" are independently selected from the group consisting of hydrogen and —$CH_3$;

(b) said hydroxy-containing organo-phosphorus compound is selected from the group consisting of:

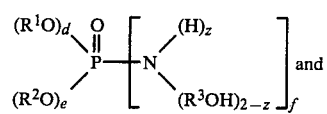     I

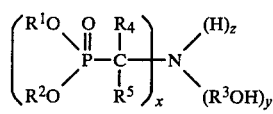     II and mixtures thereof, wherein d is an integer of from 0 to 2, e is an integer of from 0 to 2, f is an integer of from 1 to 3, and d plus e plus f equal 3; z is an integer of 0 to 1; x is an integer of 1 to 2, y is an integer of 1 to 2, and x plus y plus z equal 3; $R^1$, $R^2$, and $R^3$ are selected from the group consisting of alkyl radicals containing from about 1 to about 6 carbon atoms and haloalkyl radicals containing from about 2 to about 6 carbon atoms, provided that when $R^3$ is haloalkyl it contains at least 3 carbon atoms; $R^4$ and $R^5$ are selected from the group consisting of hydrogen, alkyl radicals, and haloalkyl radicals, wherein said radicals contain from about 1 to about 6 carbon atoms; and the total number of carbon atoms in the $R^1$, $R^2$, $R^3$, $R^4$, and $R^5$ groups does not exceed about 14; and (c) said acid is selected from the group consisting of

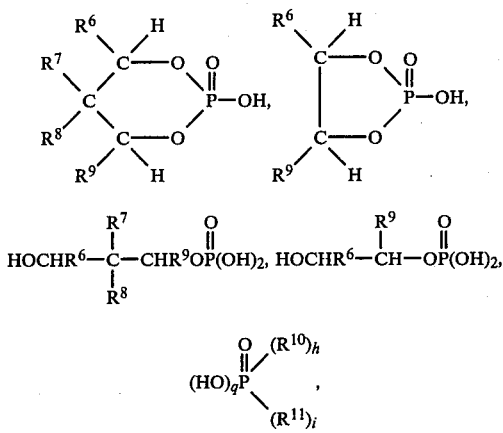

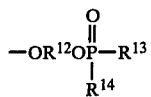

and mixtures thereof, wherein $R^6$, $R^7$, $R^8$ and $R^9$ are independently selected from the group consisting of hydrogen, alkyl of from about 1 to about 3 carbon atoms, haloalkyl of from about 1 to about 3 carbon atoms, and hydroxyalkyl of from 1 to about 3 carbon atoms, provided that the total number of carbon atoms in the $R^6$, $R^7$, $R^8$, and $R^9$ groups does not exceed about 5; wherein q is an integer of from 1 to 2, h and i are integers independently selected from the group consisting of 0, 1, and 2, and 9 plus h plus i equals 3; and wherein $R^{10}$ and $R^{11}$ are independently selected from the group consisting of alkyl of from about 1 to about 6 carbon atoms, haloalkyl of from about 1 to about 6 carbon atoms and from 1 to about 3 halogen atoms, hydroxy-polyalkyleneoxy containing 2 to 6 carbon atoms and 2 to 6 oxygen atoms, alkoxy of from about 1 to about 6 carbon atoms, hydroxyalkoxy of from about 2 to about 6 carbon atoms, haloalkoxy of from about 2 to about 6 carbon atoms and from about 1 to about 3 halogen atoms, $$-OR^{12}O\overset{O}{\underset{R^{14}}{\overset{\|}{P}}}-R^{13}$$

wherein $R^{12}$ is selected from the group consisting of alkylene of from about 2 to about 6 carbon atoms, haloalkylene of from about 3 to about 6 carbon atoms and from about 1 to about 3 halogen atoms, polyalkyleneoxy containing 2 to 6 carbon atoms and 1 to 5 oxygen atoms, and hydroxyalkylene of from 3 to about 6 carbon atoms and 1 to 4 hydroxyls, and $R^{13}$ and $R^{14}$ are independently selected from the group consisting of hydrogen, hydroxyl, alkyl of from about 1 to about 6 carbon atoms, haloalkyl of from about 1 to about 6 carbon atoms and from about 1 to about 3 halogen atoms, hydroxy-polyalkyleneoxy containing about 2 to about 6 carbon atoms and 2 to 6 oxygen atoms, alkoxy of from about 1 to about 6 carbon atoms, hydroxyalkoxy of from about 2 to about 6 carbon atoms, and haloalkoxy of from about 2 to about 6 carbon atoms and 1 to about 3 halogen atoms, provided that the total number of carbon atoms in the $R^{10}$ and $R^{11}$ groups does not exceed about 8.

2. The intumescent composition of claim 1, wherein said composition contains from about 10 to about 50 percent (by weight) of said hydroxy-containing organo-phosphorus compound, from about 10 to about 35 percent (by weight) of said organo-phosphorus acid, from about 30 to about 60 percent (by weight) of said cyclic nitrogen compound, and from about 5 to about 50 percent (by weight) of water.

3. The intumescent composition of claim 2, wherein the total number of carbon atoms in said $R^1$, $R^2$, $R^3$, $R^4$, and $R^5$ groups does not exceed about 10.

4. The intumescent composition of claim 3, wherein said composition contains from about 14 to about 40 percent (by weight) of said hydroxy-containing organo-phosphorus compound, from about 14 to about 28 percent (by weight) of said organo-phosphorus acid, and from about 8 to about 40 percent (by weight) of water.

5. The intumescent composition of claim 4, wherein said phosphorus compound is:

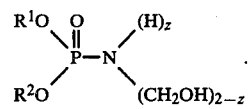

6. The intumescent composition of claim 5, wherein z is 0.

7. The intumescent composition of claim 6, wherein $R^1$ and $R^2$ are independently selected from the group consisting of alkyl radicals containing from about 1 to about 4 carbon atoms and haloalkyl radicals containing from about 2 to about 4 carbon atoms.

8. The intumescent composition of claim 7, wherein $R^1$ and $R^2$ are independently selected from the group consisting of ethyl and haloethyl.

9. The intumescent composition of claim 8, wherein $R^1$ and $R^2$ are chloroethyl.

10. The intumescent composition of claim 9, wherein said organo-phosphorus acid is 2,2-bis(bromomethyl)-3-hydroxy-1-propyl phosphoric acid.

11. The intumescent composition of claim 10, wherein a plus b plus c is 3 and X, X', and X" are —CH$_3$.

12. The intumescent composition of claim 4, wherein said phosphorus compound is:

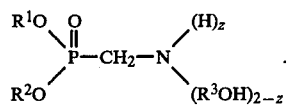

13. The intumescent composition of claim 12, wherein z is 0.

14. The intumescent composition of claim 13, wherein $R^1$ and $R^2$ are independently selected from the group consisting of alkyl radicals containing from about 1 to 4 carbon atoms and haloalkyl radicals containing from about 2 to about 4 carbon atoms.

15. The intumescent composition of claim 13, wherein $R^1$ and $R^2$ are independently selected from the group consisting of ethyl and haloethyl.

16. The intumescent composition of claim 15, wherein $R^1$ and $R^2$ are ethyl.

17. The intumescent composition of claim 16, wherein said organo-phosphorus acid is selected from the group consisting of 2,2-bis(bromomethyl)-3-hydroxy-1-propyl phosphoric acid, dibutyl hydrogen phosphate, mono-(tribromoneopentyl) phosphoric acid, 2-hydroxy-5,5-dimethyl-1,3,2-dioxophosphorinane, bis(dichloroisopropyl)phosphoric acid, bis(2-chloroethyl) phosphoric acid, chloroneopentyl phosphoric acid, and mixtures thereof.

18. The intumescent composition of claim 16, wherein a plus b plus c is 6 and X, X', and X" are —CH$_3$.

19. The intumescent composition of claim 18, wherein said organo-phosphorus acid is 2,2-bis(bromomethyl)-3-hydroxy-1-propyl phosphoric acid.

20. The intumescent composition of claim 18, wherein said organo-phosphorus acid is mono-(tribromoneopentyl)phosphoric acid.

21. The intumescent composition of claim 16, wherein a plus b plus c is 3 and X, X', and X" are —CH$_3$.

22. The intumescent composition of claim 21, wherein said organo-phosphorus acid is 2,2-bis(bromomethyl)-3-hydroxy-1-propyl phosphoric acid.

23. The intumescent composition of claim 21, wherein said organo-phosphorus acid is dibutyl hydrogen phosphate.

24. The intumescent composition of claim 21, wherein said organo-phosphorus acid is mono-(tribromoneopentyl)phosphoric acid.

25. The intumescent composition of claim 21, wherein said organo-phosphorus acid is 2-hydroxy-5,5-dimethyl-1,3,2-dioxophosphorinane.

26. The intumescent composition of claim 21, wherein said organo-phosphorus acid is bis(dichloroisopropyl)phosphoric acid.

27. The intumescent composition of claim 21, wherein said organo-phosphorus acid is bis(2-chloroethyl) phosphoric acid.

28. The intumescent composition of claim 21, wherein said organo-phosphorus acid is chloroneopentyl phosphoric acid.

29. A flame retardant article comprising an article treated with a flame-retardingly effective amount of the intumescent composition of claim 1.

30. A flame retardant article comprising an article treated with a flame-retardingly effective amount of the intumescent composition of claim 2.

31. A flame retardant article comprising an article treated with a flame-retardingly effective amount of the intumescent composition of claim 4.

32. The flame retardant article of claim 29 wherein said article is plywood.

33. The flame retardant article of claim 30 wherein said article is plywood.

34. The flame retardant article of claim 31 wherein said article is plywood.

35. The flame retardant article of claim 29 wherein said article is filter paper.

36. The flame retardant article of claim 30 wherein said article is filter paper.

37. The flame retardant article of claim 31 wherein said article is filter paper.

38. A flame retardant article comprising thin layers of wood bonded together with an adhesively-effective and flame-retardingly effective amount of the intumescent composition of claim 1.

39. A flame retardant article comprising thin layers of wood bonded together with an adhesively-effective and flame-retardingly effective amount of the intumescent composition of claim 2.

40. A flame retardant article comprising thin layers of wood bonded together with an adhesively-effective and flame-retardingly effective amount of the intumescent composition of claim 4.

41. A flame retardant article comprising fibers bonded together with an adhesively-effective and fire-retardingly effective amount of the intumescent composition of claim 1.

42. A flame retardant article comprising fibers bonded together with an adhesively-effective and fire-retardingly effective amount of the intumescent composition of claim 2.

43. A flame retardant article comprising fibers bonded together with an adhesively-effective and fire-retardingly effective amount of the intumescent composition of claim 4.

* * * * *

UNITED STATES PATENT AND TRADEMARK OFFICE
CERTIFICATE OF CORRECTION

PATENT NO. : 4,345,002
DATED : August 17, 1982
INVENTOR(S) : Ray E. Smith, et al.

It is certified that error appears in the above-identified patent and that said Letters Patent are hereby corrected as shown below:

Col. 4, line 15, "and f" should be --plus f--.
Col. 4, line 69, "atom" should be --atoms--.
Col. 5, line 19, "B 6 oxygen" should be --6 oxygen--.
Col. 6, line 14, "comound" should be "compound--.

Col. 6, line 29 in diagram, "$(R^3OH)_{2-z}$" should be --$(CH_2-OH)_{2-z}$.

Col. 10, line 11, "1,3,2-dioxaphosphospholane-2" should be --1,3,2-dioxaphospholane-2--.
Col. 10, line 32, "dioxaphosphorinae" should be --dioxaphosphorinane--.
Table II - heading, "g" should be --q--.
Col. 17, line 5, "Cyanamide" should be --Cyanamid--.
Col. 18, line 14, "treated" should be --tested--.
Col. 18, Table III, in heading, "16*" should be --16**--.
Col. 24, line 3, "containining" should be --containing--.
Col. 24, line 3, "$8^0$" should be --80--.
Col. 26, line 2, "B 50.1%" should be --50.1%--.
Col. 26, line 13, "comprehende" should be --comprehended--.

Signed and Sealed this

Fifteenth Day of March 1983

[SEAL]

Attest:

GERALD J. MOSSINGHOFF

Attesting Officer

Commissioner of Patents and Trademarks